United States Patent [19]

Rogic' et al.

[11] 4,240,966

[45] Dec. 23, 1980

[54] CYCLIC KETALS OF α-OXIMINO-CYCLOALKANONES

[75] Inventors: Milorad M. Rogic', Whippany; Michael D. Swerdloff, Parsippany; Timothy R. Demmin, Morris Plains, all of N.J.

[73] Assignee: Allied Chemical Corporation, Morris Township, Morris County, N.J.

[21] Appl. No.: 968,934

[22] Filed: Dec. 13, 1978

Related U.S. Application Data

[60] Division of Ser. No. 807,692, Jun. 17, 1977, abandoned, which is a division of Ser. No. 600,666, Jul. 31, 1975, Pat. No. 4,045,422, which is a continuation-in-part of Ser. No. 460,836, Apr. 15, 1974, abandoned.

[51] Int. Cl.$^3$ .................. C07D 317/44; C07D 317/10
[52] U.S. Cl. ...................... 260/340.5 R; 260/340.9 R
[58] Field of Search ................ 260/340.9 R, 566 A, 260/340.5 R

[56] References Cited

U.S. PATENT DOCUMENTS

| | | | |
|---|---|---|---|
| 3,059,018 | 10/1962 | Johnson et al. | 260/566 A |
| 3,467,673 | 9/1969 | Sallay | 260/340.9 R |
| 3,758,581 | 9/1973 | Fuhrmann et al. | 260/340.9 R X |
| 3,803,231 | 4/1974 | Fuhrmann et al. | 260/566 A |
| 4,045,422 | 8/1977 | Rogic et al. | 260/340.9 R X |

OTHER PUBLICATIONS

Chem. Abstracts, 47:2714h.
Rasmussen et al., J. Org. Chem., vol. 39, (17), pp. 2558–2561, (1974).

*Primary Examiner*—Ethel G. Love
*Attorney, Agent, or Firm*—Robert A. Harman

[57] ABSTRACT

This invention describes novel cyclic ketals of α-oximinoketones and methods for the preparation of these compounds.

1 Claim, No Drawings

CYCLIC KETALS OF α-OXIMINO-CYCLOALKANONES

This is a division of Application Ser. No. 807,692, filed June 17, 1977, now abandoned, as a division of Application Ser. No. 600,666 filed July 31, 1975 (now U.S. Pat. No. 4,045,422) which is itself a continuation-in-part of Application Ser. No. 460,836 filed Apr. 15, 1974 (now abandoned).

FIELD OF THE INVENTION

This invention describes novel cyclic ketals of various α-oximinoketones and methods for the preparation of these compounds.

Beckman fragmentation of these novel ketals of α-oximino ketones, provides the corresponding alkyl ω-cyanoalkanoates which are convenient intermediates for the production of either cyclic lactams or polyamides and amino acids.

SUMMARY OF THE INVENTION

The novel ketals of α-oximinoketones described in the present invention may be characterized by the following formula:

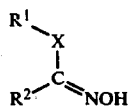

wherein: $R^1$ and $R^2$ together represent a part of the $C_5-C_{12}$ cyclic ring structure; and X is a member of the group consisting of:

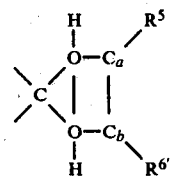

wherein $R^5$ and $R^6$ are independently hydrogen, phenyl, $C_1-C_{10}$ alkyl, or in combination with $C_a$ and $C_b$ form a cyclohexyl radical.

Illustrative are:

6-oximino-1,4-dioxaspiro[4,5]decane

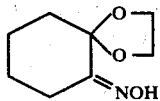

6-oximino-2,3,8-trimethyl-1,4-dioxaspiro-[4,5]decane

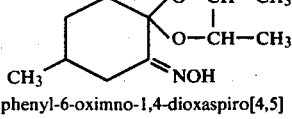

2-phenyl-6-oximno-1,4-dioxaspiro[4,5]decene

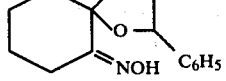

2'-oximinohexahydraspiro[1,3-benzodioxole-2,1'-cyclohexane]

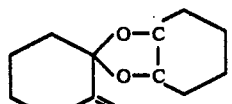

2-isopropyl-6-oximino-1,4-dioxaspiro[4,5]decane

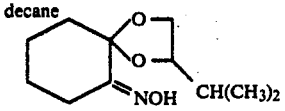

2-t-butyl-6-oximino-1,4-dioxaspiro[4,5]decane

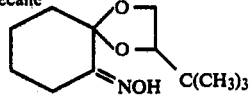

In addition to producing these novel α-oximinoketals by nitrosating with alkyl nitrites and isomerizing, it is possible to perform the desired nitrosation using at least one molar equivalent each of a nitrosyl halide, a base and an alcohol of the formula $R^4OH$ where $R^4$ is as previously defined; and isolating the desired product.

The novel cyclic ketals of α-oximinocyclohexanone disclosed herein are similarly prepared by nitrosating, in an inert solvent a cyclohexanone compound of the formula

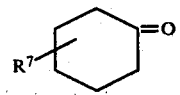

wherein $R^7$ is a $C_1-C_4$ alkyl radical, with at least one molar equivalent of each of a nitrosyl halide, an acid, and a vicinal diol of the formula

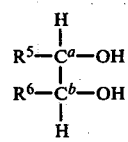

where $R^5$ and $R^6$ are as previously defined; neutralizing the acidic intermediate thus produced; and isolating the resulting cyclic ketal of α-oximinocyclohexanone.

DESCRIPTION OF THE PREFERRED EMBODIMENTS

The synthesis of the novel cyclic ketal derivatives of α-oximinocyclohexanone is achieved by the nitrosation in the presence of an inert solvent of a cyclohexanone compound of the formula

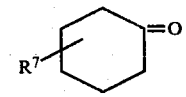

wherein $R^7$ is as previously defined, with at least one molar equivalent of each of a nitrosyl halide, an acid, and a vicinal diol of the formula

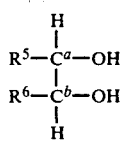

where $R^5$ and $R^6$ are as previously defined, neutralizing the acid salts thus formed; and isolating the desired product. Schematically, the reaction proceeds as follows:

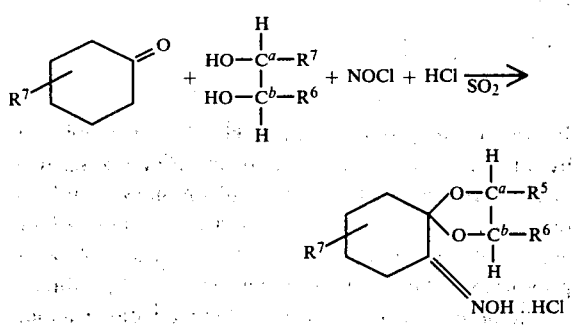

wherein $R^5$, $R^6$, $R^7$ and $C^a$ and $C^b$ are as previously defined. The nitrosation reaction may be carried out either with a nitrosyl halide, preferably nitrosyl chloride, or with an alkyl nitrite in the presence of hydrogen halide to produce the nitrosyl halide in situ. In either case, at least one molar equivalent nitrosating agent, preferably 1.10–1.50 molar equivalents nitrosating agent, is employed together with at least one additional mole, preferably one to two additional moles strong acid, preferably HCl. This reaction may be carried out in an inert solvent, preferably liquid sulfur dioxide. The reaction temperature may vary between about $-70°$ and $+50°$ C. with preferred range of $-20°$ to $+25°$ C. at pressures of one atmosphere to 200 psi.

The nitrosation is accomplished either by introducing the nitrosyl halide into a solution of the cyclohexanone in the solvent in the presence of an acid catalyst and the vicinal diol, or by addition of an alkyl nitrite to the same solution containing an additional equivalent of acid. In the latter case, the alkyl nitrite may be either derived from the corresponding vicinal diol or may be selected in such a way as to assure that the generated alcohol would not adversely compete with the glycol in the ketal formation. A suitable alkyl nitrite, for example, would be t-butyl nitrite.

The reaction is usually complete after addition of all the nitrosating agent; however, the reaction period may be extended with no deleterious results. The product may be isolated by removal of the solvent and any excess acid in vacuo at temperatures between about $-70°$ and $+10°$ C., preferably between $-10°$ and $+5°$ C., followed by neutralization of the acid salt in a solution of a solvent such as chloroform containing a suitable base such as anhydrous ammonia, ammonium hydroxide, pyridine, triethylamine, a solution of sodium methoxide, sodium hydroxide or moist sodium bicarbonate. The cyclic ketal thus produced is then isolated by filtering to remove the salts of neutralization and the solvent is then evaporated. The crude cyclic ketal derivative of α-oximinocyclohexanone may then be purified either by crystallization or by column chromatography. The synthesis of the novel cyclic ketal derivatives of α-oximinocyclohexanone has also been achieved by the nitrosation in the presence of an inert solvent of a cyclohexanone ketal of the formula:

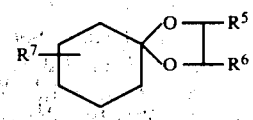

wherein $R^5$, $R^6$ and $R^7$ are as previously defined, with at least one molar equivalent of a nitrosyl halide and preferably one molar equivalent of an acid, neutralizing the acid salts thus formed; and isolating the desired product. Schematically, the reaction proceeds as follows:

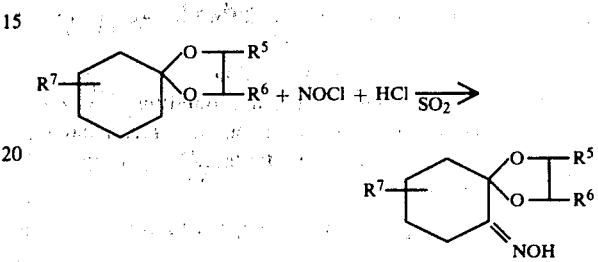

wherein $R^5$, $R^6$ and $R^7$ are as previously defined.

The invention will be further illustrated by the following Examples.

EXAMPLE 1

Production of 6-oximino-1,4-dioxaspiro[4,5]decane

A three-neck 500 ml. flask equipped with a serum capped inlet, a mechanical stirrer, inlets for the introduction of sulfur dioxide and hydrogen chloride, and a dry ice condenser protected with a nitrogen bubbler, was placed in a dry ice/acetone bath at $-30°$. A sulfur dioxide cylinder was connected to one inlet and about 125 ml. of sulfur dioxide was distilled into the flask. The stirrer was started and ethylene glycol (100 mmole, 5.60 ml.) was added by a syringe. Dry hydrogen chloride (125 mmole) was slowly bubbled into the solution and then cyclohexanone (100 mmole, 10.4 ml.) was added by a syringe. The hydrogen chloride inlet was removed and replaced with an inlet connected through a stopcock to a precooled flask containing 125 mmole (8.16 g.) of liquid nitrosyl chloride. The dry ice/acetone bath was removed and the reaction solution allowed to come to reflux (2°–10°). The stopcock on the nitrosyl chloride flask was then opened and the flask was gently warmed to allow the slow introduction of nitrosyl chloride vapors above the surface of the reaction solution. The addition was continued until the solution became pale orange (45 min.). The solution was stirred for another 15 min. and then poured into a 500 ml. predried and precooled flask. The reaction vessel was washed once with chloroform which was added to the sulfur dioxide solution. The flask was connected to a rotary evaporator and the solution was evaporated in vacuo at $-20°$. The last traces of sulfur dioxide were removed by the further addition of about 75 ml. of cold chloroform and re-evaporation. The resulting pale yellow oil was washed with the aid of chloroform into a 250 ml. beaker containing a stirring bar. The solution was diluted with chloroform to 150 ml., the stirrer was started, and the solution was neutralized to about pH 8 with either a paste of sodium bicarbonate or ammonia gas. The solution was dried by adding anhydrous magnesium sulfate and stirring for an additional few minutes. The salts were removed by filtration and the chloroform solution was concentrated to give 16.3–18.3 g. of a brown, viscous oil. Analysis of this oil by nmr indicated it to be about 80–90% 6-oximino-1,4-dioxaspiro[4,5]decane and about 10–20% 2-hydroxy-ethyl-6-oximinohexanoate. The product was isolated by either crystallization, distillation or column chromatography, m.p. 97°–98°.

EXAMPLES 2–7

The procedure of Example 1 has also been used to produce the following novel cyclic ketals from a cyclohexanone.

| Example | Cyclohexanone | Diol | Product | m.p. (°C.) | Yield (%) |
|---|---|---|---|---|---|
| 2 | cyclohexanone | 1,2-propane-diol | 2-methyl-6-oximino 1,4-dioxaspiro-[4,5]decane | 115–117 | 70 |
| 3 | cyclohexanone | 3-methyl-1,2-butane-diol | 2-isopropyl-6-oximino-1,4-dioxaspiro[4,5]-decane | 62 | 60 |
| 4 | cyclohexanone | 1-phenyl-1,2-ethane-diol | 2-phenyl-6-oximino-1,4-dioxaspiro[4,5]-decane | 130–132 | 60 |
| 5 | cyclohexanone | cis-1,2-cyclo-hexane-diol | 2'-oximinohexa-hydrospiro[1,3-benzodioxole-2,1'-cyclohexane] | 157–159 | 25 |
| 6 | 4-t-butyl-cyclohexanone | 1,2-ethane-diol | 8-t-butyl-6-oximino-1,4-dioxa-spiro[4,5]-decane | 153–154 | 65 |
| 7 | 4-t-butyl-cyclohexanone | 1,2-pro-pane diol | 8-t-butyl-2-methyl-6-oximino-1,4-dioxaspiro-[4,5]-decane | 119–125 | 50 |

EXAMPLES 8–9

The procedure of Example 1 can also be employed to produce the following novel cyclic ketals from a cyclohexanone.

| Example | Cyclohexanone | Diol | Product |
|---|---|---|---|
| 8 | 4-methyl cyclohexanone | 2,3-butanediol | 6-oximino-2,3,8-trimethyl-1,4-dioxaspiro[4,5]decane |
| 9 | 3-phenyl-cyclohexanone | 2,2-dimethyl-cis-3,4-butane-diol | 3-5-butyl-6-oximino-9-phenyl-1,4-dioxaspiro[4,5]-decane |

EXAMPLE 10

Production of 6-oximino-1,4-dioxaspiro[4,5]decane

The same procedure as in Example 1 was used except 1,4-dioxaspiro[4,5]decane (14.2 g., 100 mmole) was used in place of the cyclohexanone and ethylene glycol.

EXAMPLES 11–12

The same method employed as in Example 1 can be used to produce the following novel compounds.

| Example | Cyclohexanone | Diol | Product |
|---|---|---|---|
| 13 | cyclohexanone | 1,2-diphenyl-1,2-ethanediol | 2,3-diphenyl-6-oximino-1,4-dioxa-spiro[4,5]decane |
| 14 | 4-t-butyl-cyclohexanone | 1,2-propane-diol | 2-methyl-8-5-butyl-6-oximino-1,4-dioxa-spiro[4,5]decane |

We claim:
1. Cyclic alpha-oximinocyclohexanone ketals characterized by the formula

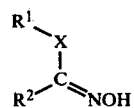

wherein: together $R^1$, $R^2$ are hydrocarbon moieties forming part of a $C_6$ monocyclic structure and X is

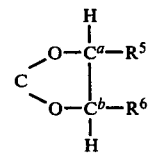

wherein $R^5$, $R^6$ independently are hydrogen, phenyl, $C_1$–$C_{10}$ alkyl or in combination with $C^a$, $C^b$ form a cyclohexyl radical.

* * * * *